United States Patent [19]
Zhang et al.

[11] Patent Number: 5,675,048
[45] Date of Patent: *Oct. 7, 1997

[54] DUAL REGENERATION ZONE SOLID CATALYST ALKYLATION PROCESS

[75] Inventors: Scott Yu-Feng Zhang, Carol Stream; Christopher David Gosling, Roselle; Paul Alvin Sechrist, Des Plaines; Gregory A. Funk, Carol Stream, all of Ill.

[73] Assignee: UOP, Des Plaines, Ill.

[*] Notice: The term of this patent shall not extend beyond the expiration date of Pat. No. 5,489,732.

[21] Appl. No.: 597,047

[22] Filed: Feb. 5, 1996

Related U.S. Application Data

[63] Continuation-in-part of Ser. No. 323,437, Oct. 14, 1994, Pat. No. 5,489,732.
[51] Int. Cl.$^6$ .................... C07C 2/68; C07C 2/58
[52] U.S. Cl. .................... 585/467; 585/722
[58] Field of Search .................... 585/467, 449, 585/450, 451, 464, 719, 716, 722

[56] References Cited

U.S. PATENT DOCUMENTS

| | | |
|---|---|---|
| 3,851,004 | 11/1974 | Yang . |
| 4,008,291 | 2/1977 | Zabransky et al. . |
| 4,028,430 | 6/1977 | Stine et al. . |
| 4,139,573 | 2/1979 | Carson . |
| 4,973,780 | 11/1990 | Johnson et al. . |
| 5,157,196 | 10/1992 | Crossland et al. .................... 585/720 |
| 5,489,732 | 2/1996 | Zhang et al. .................... 585/467 |

*Primary Examiner*—Elizabeth D. Wood
*Assistant Examiner*—Tanaga A. Boozer
*Attorney, Agent, or Firm*—Thomas K. McBride; John F. Spears Jr.

[57] ABSTRACT

Hydrocarbons are alkylated in a fluidized riser-reactor using a solid catalyst which is regenerated within the process by contact with hydrogen. The alkylation and regeneration steps are separated to prevent the admixture of hydrogen and any olefins present in the process. Two separate modes of regeneration are performed simultaneously on different portions of the catalyst: a partial liquid-phase hydrogenative regeneration at reaction conditions and a high temperature (complete) liquid-phase hydrogenative regeneration.

11 Claims, 2 Drawing Sheets

DUAL REGENERATION ZONE SOLID CATALYST ALKYLATION PROCESS

CROSS REFERENCE TO RELATED APPLICATION

This application is a continuation-in-part of our prior application Ser. No. 08/323,437 filed 14 Oct. 1994 and now U.S. Pat. No. 5,489,732.

BACKGROUND OF THE INVENTION

1. Field of the Invention

The invention relates to a hydrocarbon conversion process. The invention specifically relates to the alkylation of hydrocarbons such as aromatics or paraffins to produce useful chemicals and motor fuel. The invention is primarily directed to a process for the solid bed alkylation of isobutane to produce $C_8$ isoparaffins useful as motor fuel blending components.

2. Related Art

Large amounts of high octane gasoline are produced by the alkylation of isobutane with butenes. Likewise, large amounts of valuable aromatic hydrocarbons including cumene, ethylbenzene and $C_{16}$–$C_{21}$ linear alkylaromatics are produced by the alkylation of benzene with olefins of the appropriate carbon number. The variety of feed reactants and the passage of time has led to the development of a number of effective alkylation technologies which are employed in large scale commercial facilities.

One of the most widely used processes for the production of motor fuel is HF alkylation as described in U.S. Pat. No. 4,139,573 issued to D. B. Carson, which provides an overview of the HF alkylation process. One of the advantages of the use of liquid-phase HF as a catalyst is its resistance to deactivation, and the relative ease with which a slipstream may be removed from an onstream reaction zone for "regeneration". The HF itself is not chemically changed during use but various organic reaction byproducts such as "acid soluble oils" (ASO) accumulate in the liquid-phase HF and are removed during this regeneration.

Regeneration is also necessary for all solid bed motor fuel alkylation catalysts developed to date since they tend to suffer from a high deactivation rate. Deactivation of solid catalysts is due to different, possibly multiple, causes from those encountered with liquid HF as a catalyst and usually includes some accumulation of hydrocarbonaceous deposits on the catalyst.

A common method of regenerating catalysts is by combustion of organic deposits. This is often not desired or possible for alkylation catalysts. U.S. Pat. No. 3,851,004 to C. L. Yang describes an alternative method for regenerating a solid bed alkylation catalyst comprising a hydrogenation component on a zeolitic support which comprises contacting the catalyst with a hydrogen-containing liquid-phase saturated hydrocarbon.

Any interruption in the operation of the reaction zone to regenerate or replace catalyst is undesirable. Certain operating benefits are provided to any process by an ability to operate in a continuous manner, which makes it desirable to find a means to regenerate or replace the catalyst while the reaction zone is kept in use. U.S. Pat. No. 4,973,780 issued to R. C. Johnson et al describes a moving bed benzene alkylation process in which catalyst is continuously or periodically replaced with regenerated catalyst to provide countercurrent catalyst-reactant flows. Cocurrent flow with catalyst added to the bottom of the reactor is also disclosed.

It has also been proposed to provide continuous operation by simulating the movement of the catalyst through the reaction and regeneration zones. U.S. Pat. Nos. 4,008,291 to R. F. Zabransky et al. and 4,028,430 to L. O. Stine et al. describe the use of simulated countercurrent operations to perform a number of alkylation reactions including the production of motor fuel. These references provide separate reaction and catalyst reactivation zones, with an external regenerant stream being employed for the reactivation. In both references the effluent of the reaction zone is withdrawn from the alkylation zone immediately upon its exit from the reaction zone. These references also teach the use of a "pump around" stream to complete the simulation and provide a continuous liquid loop.

Finally, U.S. Pat. No. 5,157,196, issued to C. S. Crossland et al. describes a moving bed paraffin alkylation process which employs a plug flow reaction zone in which the catalyst moves upward to a disengaging zone. Used catalyst from the disengaging zone is passed into a wash zone.

BRIEF SUMMARY OF THE INVENTION

The invention is a fluidized process for the alkylation of hydrocarbons. The invention provides a continuous reaction zone which is not interrupted for the periodic regeneration of catalyst. The invention also eliminates the need to perform motor fuel alkylation reactions using volatile and hazardous liquid phase sulfuric or hydrofluoric acid. The invention is characterized by the use of a fluidized riser-type reaction zone with the upper end of the reaction zone discharging into a separate zone in which the reactants and products are separated from used catalyst and the used catalyst is then stripped and recirculated to the riser. A first portion of the used catalyst is partially or mildly regenerated by hydrogenative washing while a smaller second portion is drawn off for full hydrogenative regeneration in a second higher temperature regeneration zone. It has now been discovered that this full regeneration can be performed using liquid-phase hydrocarbons containing dissolved hydrogen.

One broad embodiment of the invention may be characterized as a process for the alkylation of a feed hydrocarbon which comprises the steps: passing a first catalyst stream, comprising regenerated catalyst withdrawn from a first regeneration zone, and a feed stream comprising the feed hydrocarbon and an alkylating agent into a vertical fluidized reaction zone maintained at reaction conditions including a pressure sufficient to maintain liquid-phase conditions and a temperature of 0°–170° F. and producing a reaction zone effluent stream comprising used catalyst, the feed hydrocarbon and a product hydrocarbon; discharging the reaction zone effluent stream into a separation zone in which used catalyst is separated from liquid phase product hydrocarbon and thereby forming a liquid-phase separation zone effluent stream comprising the feed and product hydrocarbons, with the thus separated used catalyst descending downward within the separation zone; transferring a major first aliquot portion of the used catalyst downward through the liquid-phase first regeneration zone operated at conditions essentially equal to those maintained in the riser-reaction zone and wherein the used catalyst is contacted with the feed hydrocarbon and dissolved hydrogen to form partially regenerated catalyst, and removing said partially regenerated catalyst from the regeneration zone as a second catalyst stream; transferring a smaller aliquot second portion of the used catalyst from the separation zone into a liquid-phase second regeneration zone operated at a pressure substantially equal to the pressure in the riser-reaction zone and wherein the used catalyst is contacted with a liquid-phase regeneration stream comprising dissolved hydrogen at high temperature liquid-phase regeneration conditions, including a temperature at least about 50° F. above the outlet temperature of the reaction zone, and withdrawing catalyst from the second regeneration zone as a third catalyst stream; admixing the third catalyst stream with partially regenerated catalyst; and recovering the product hydrocarbon from the separation zone effluent stream.

DETAILED DESCRIPTION AND PREFERRED EMBODIMENTS

Figure 1:
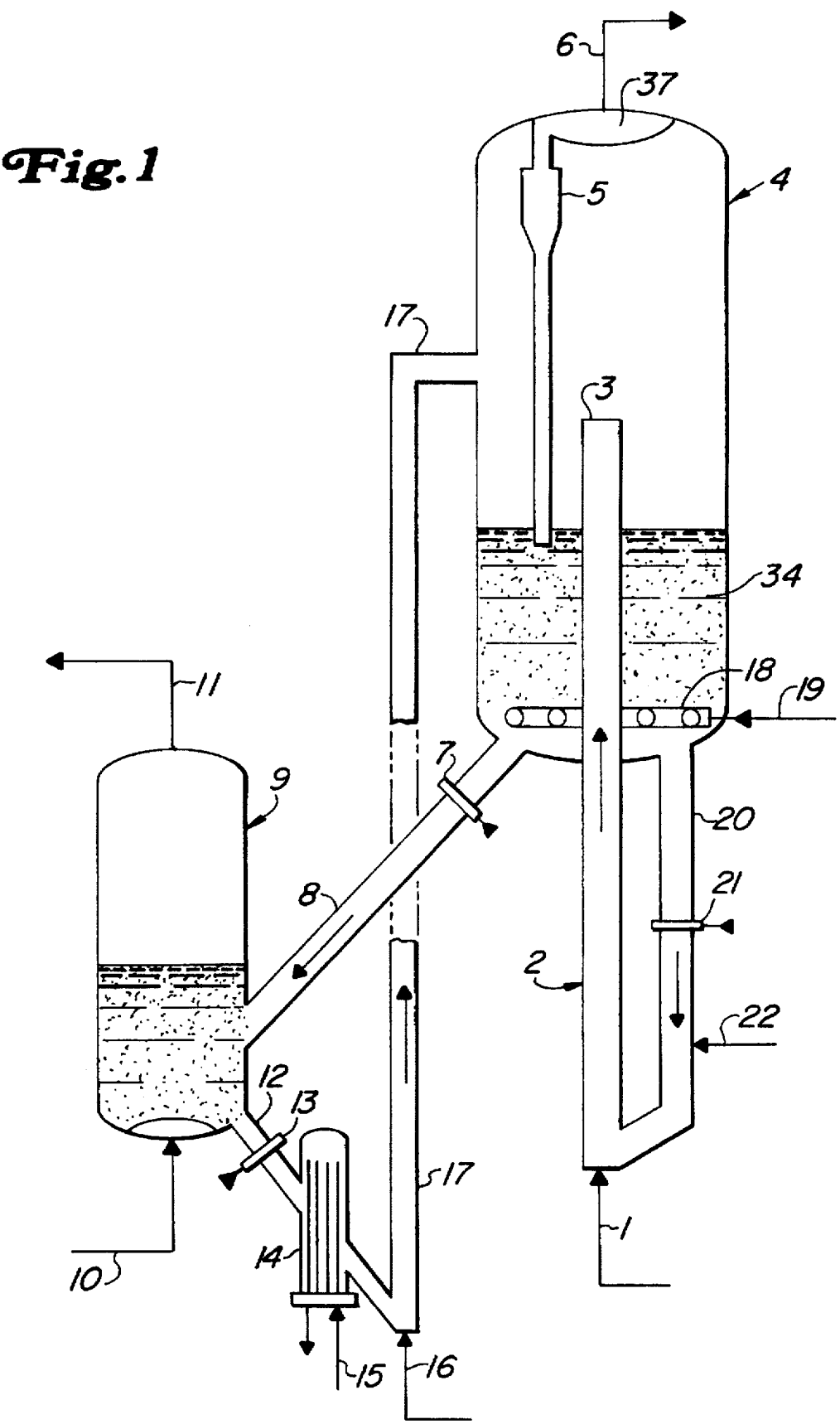
FIG. 1 is a simplified diagram illustrating one embodiment of the invention in which the riser-reactor 2 discharges into a large separation zone 3, with the flow of used catalyst being divided between a low temperature regeneration zone 5 and a high temperature regeneration zone 12, in both of which the catalyst is subjected to liquid-phase regeneration.

Hydrocarbon alkylation is widely used in the petroleum refining and petrochemical industries to produce a variety of useful acyclic and cyclic hydrocarbon products which are consumed in motor fuel, plastics, detergent precursors, and petrochemical feedstocks. Much of the installed base of alkylation capacity uses liquid phase hydrofluoric acid, generally referred to as HF, as the catalyst. The use of HF in these applications has a long record of highly dependable and safe operation. However, the potential damage from an unintentional release of any sizeable quantity of HF and the need to safely dispose of some byproducts produced in the process has led to an increasing demand for alkylation process technology which does not employ liquid phase HF as the catalyst.

Numerous alkylation catalysts have been described in the open literature. However, those that we have knowledge of all appear to suffer from high deactivation rates when employed at commercially feasible conditions. While some catalysts have a sufficiently useful lifetime to allow the performance of alkylation, the rapid change in activity results in a change in product composition and also requires the periodic regeneration of the catalyst with the accompanying removal of the reaction zone from operation. It is very desirable to provide a continuous process for alkylation which is not subjected to periodic reaction zone stoppages or variation in the product stream composition.

It is an objective of this invention to provide an alkylation process which does not employ liquid phase HF as the catalyst. It is a further objective of the subject invention to provide a motor fuel alkylation process which utilizes a solid catalyst. It is a specific objective of the invention to provide a continuous solid catalyst alkylation process for the production of motor fuel blending hydrocarbons. A further objective of the subject invention is to provide a commercially viable continuous motor fuel alkylation process which delivers a uniform quality and quantity of product and which employs a regenerable solid alkylation catalyst.

The subject process achieves these objectives by the use of a unique flow scheme in which a riser-type reactor delivers the product hydrocarbons and used catalyst to a liquid phase separation zone from which catalyst is removed for division between one of two regeneration zones operated at different conditions.

The hydrocarbon feedstock to the subject process may be essentially any hydrocarbon which is retained as an easily flowable liquid phase material at the conditions employed in the reaction and mild regeneration zones and which may be alkylated via solid catalyst at the conditions maintained in the riser reaction zone. The feed hydrocarbon may therefore be an aromatic hydrocarbon such as benzene or toluene. This feed hydrocarbon or substrate is often reacted with an alkylating agent comprising an acyclic light olefin such as ethylene, propylene or butylene to produce such chemicals as ethylbenzene and cumene. A large amount of benzene is alkylated with higher carbon number olefins having from about 10 to about 15 carbon atoms per molecule to produce linear alkyl benzenes which are then sulfonated to produce detergents. For motor fuel production the preferred feed hydrocarbons are light paraffinic hydrocarbons such as the butanes. An especially preferred paraffinic feed hydrocarbon is isobutane.

The entering feed hydrocarbon is typically alkylated with a linear olefin having from 2 to about 15 carbon atoms per molecule. The feed hydrocarbon may also be reacted with an alkylating agent chosen from a variety of compounds other than olefins including monohydric alcohols if the catalyst is compatible with alcohols. Zeolitic catalysts are suitable for this function. Examples of the alcohols which may be employed as the alkylating agent include ethanol and methanol. For instance, methanol is widely described in the literature as being useful in the paraselective methylation of benzene and toluene.

An overview of the operation of the subject process may be obtained by reference to the Drawing. As shown in the Drawing a hydrocarbon feedstream containing the olefinic hydrocarbon which is to be consumed in the reaction, which for purposes of illustration is assumed to be a $C_4$ olefin, enters the process through line 1. This feedstream may contain other hydrocarbons such as paraffinic diluents and/or the feed hydrocarbon which is to take part in the alkylation reaction. In the specific instance shown in the Drawing, the feedstream of line 1 contains isobutane in addition to the butenes. This feedstream fluidizes and lifts regenerated catalyst entering the bottom of the riser 2 from line 9 and carries the alkylation catalyst upward through the riser. While the catalyst is being transported upward through the riser, it is promoting the alkylation reaction between the butenes and isobutane resulting in the production of various $C_8$ paraffinic hydrocarbons. Additional quantities of butene can be added at intermediate points along the length of the reactor 2 through lines 10 and 11 to reduce the amount of olefin added at the reactor inlet, thus increasing the paraffin to olefin ratio, or to produce more alkylate. The mixture of liquid phase hydrocarbons and the catalyst continues to move upward through the riser reaction zone 2, although the two phases will not necessarily move at equal rates, with the relative rates being dependent on physical characteristics of the catalyst particles. At the upper end of the riser reaction zone, the flowing stream of catalysts and hydrocarbons is diverted into an uppermost separation zone of the catalyst maintenance or regeneration section of the process. This separation zone 3 may be a hydrocyclone which functions to separate the entering mixed phase stream into an essentially solids-free hydrocarbon product stream removed from the process through line 4 and a quantity of recovered catalyst which settles to the bottom of the separation zone 3. Other catalyst disengaging systems used on fluidized systems can be used.

The majority of the catalyst entering the separation zone 3 begins to slowly descend through the larger opening provided at the bottom of the separation zone and enters a transitional washing and mild regeneration zone 5 operated at the same conditions as the reaction zone. This procedure is intended to promote thorough removal of the product hydrocarbon from the catalyst. A number of optional louvers 18 may extend into the internal volume of the cylindrical wash zone 5 to agitate the descending catalyst and ensure admixture and thorough washing of the catalyst by a slowly rising stream of isobutane. The catalyst exits the bottom of the wash zone 5 and is collected in a flow buffering and stripping zone 6. The flow buffering zone 6 allows for flexibility of operation and also provides additional residence time during which the used catalyst is contacted with the gently upflowing hydrogen-containing isobutane charged to this overall catalyst renewal column through line 7. At the bottom of this regeneration column, a stream of hydrogen-free isobutane is charged through line 20 to flush the catalyst free of hydrogen. The thus washed and partially regenerated catalyst is removed from zone 6 through line 8 at a rate controlled by the slide valve 17 in line 9.

A second, smaller portion of the catalyst which has just been separated from the reactants in zone 3 is withdrawn through line 22 at a rate controlled by a slide valve 21 and passed into a hydrogenative regeneration zone 12. For operational simplicity the catalyst flow through line 10 may not be continuous and catalyst move in batches. A continuous flow would be desirable if the downstream regeneration zone 12 can function with a continuous flow. In zone 12 the catalyst is retained in a fixed (nonfluidized) dense bed which is maintained in contact with flowing liquid phase relatively high temperature isobutane having hydrogen dissolved therein. This liquid phase regeneration stream enters the process through line 13 and is removed through line 14. The regeneration zone 12 is operated at essentially the same pressure as the rest of the overall alkylation process but at a relatively elevated temperature of about 150°–250° F. The slide valves shown in the Drawing are intended to control catalyst flow rather than to provide liquid tight seals which would allow the establishment of radically different operating conditions. Furthermore, the slide valve 21 may prove to be unneeded as the flow rate of catalyst into and through the regeneration zone 12 can be controlled at least in part by slide valve 16 on line 15. Slide valve 21 will still be useful in isolating the regeneration zone to minimize the flow of hydrogen containing liquid into the separation zone 3. These valves are also useful in controlling the relative flow rates in the two regeneration zones.

Regenerated catalyst is withdrawn from the regeneration zone 12 through line 15 and flushed with hydrogen-free isobutane from line 23 at a rate controlled by valve 16. It is then admixed with the catalyst being withdrawn from zone 6 via line 8. These two streams of regenerated catalyst are flushed with hydrogen-free isobutane from line 19 to thereby form the catalyst charged to the bottom of riser reaction zone 2.

In an embodiment not shown in the drawing, the regenerated catalyst from the high temperature regeneration zone 12 is passed into the low temperature regeneration zone 5 rather than being admixed with catalyst withdrawn from zone 5.

Figure 2:
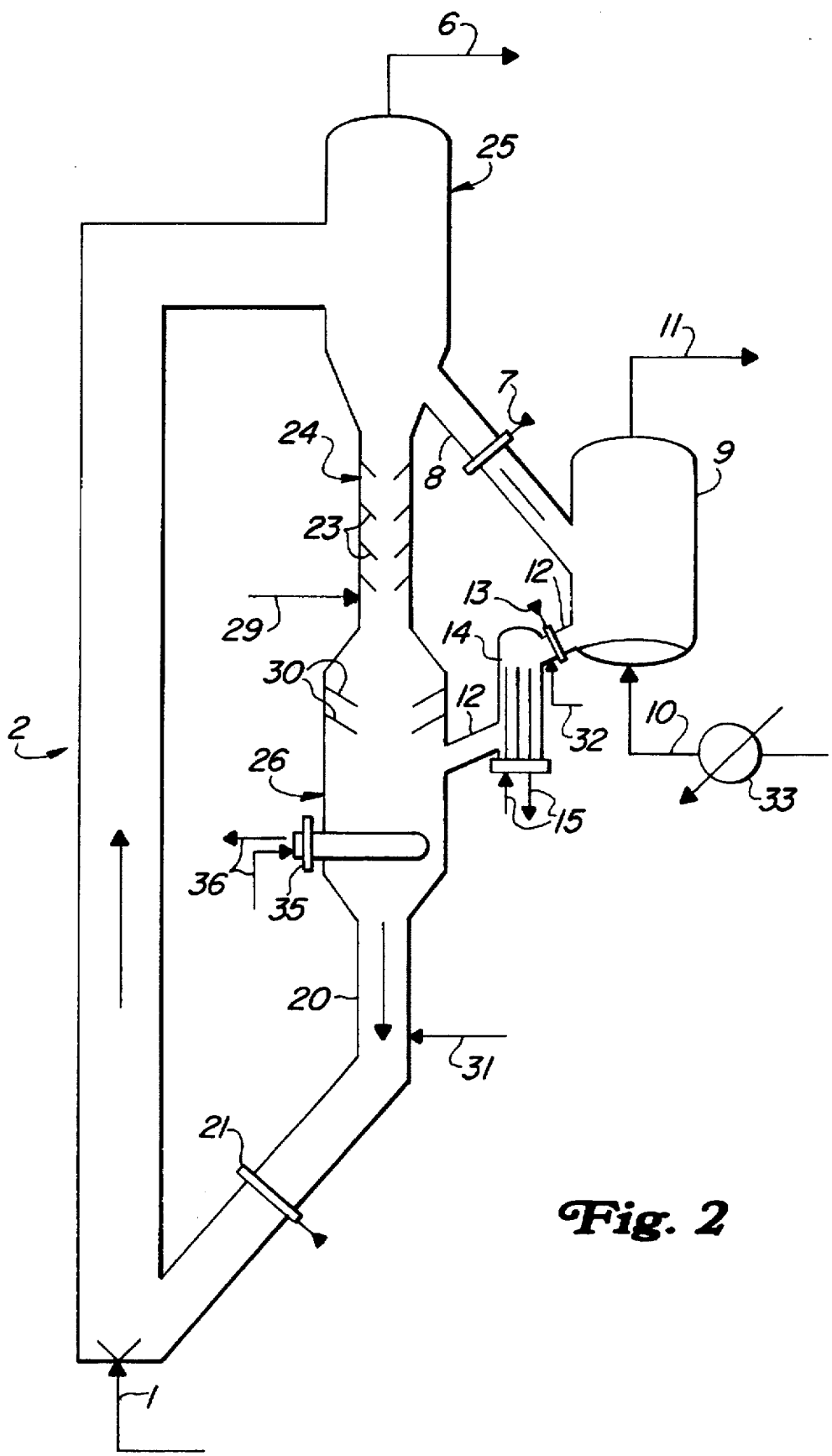
FIG. 2 illustrates a different embodiment of the invention in which regenerated catalyst from the high temperature regeneration zone 42 is mixed with used catalyst by discharge into the vessel 30 containing the low temperature regeneration zone.

FIG. 2 illustrates an alternative arrangement of the process flow of the subject new embodiment of our invention. In this process flow the feed mixture containing the olefinic hydrocarbon, preferably diluted with the paraffinic feed hydrocarbon enters the process through line 24 and immediately joins catalyst from line 34 and passes upward through the riser-reaction zone 25. The admixture of solid catalyst and reactants passes upward through the riser with the catalyst promoting the reaction of the olefin and the feed paraffin to produce branched chain motor fuel alkylate. The admixture of product alkylate hydrocarbon, residual feed hydrocarbon and used catalyst exits the top 26 of the riser reaction zone and is discharged into a large overall vessel 30. The upper portion of the vessel forms a separation zone in which by gravitational action at least a partial separation of the solid catalyst particles and the liquid hydrocarbons takes place. The liquid phase then enters one or more hydrocyclones 27 intended to ensure a complete separation of catalyst from the liquid. The liquid then flows into a plenum chamber 28 designed to accommodate the attachment of multiple hydrocyclones prior to being removed from the process through line 29 for passage into the appropriate fractional distillation or other product recovery facilities.

A dense bed of catalyst 31 is allowed to accumulate in the lower portion of the overall vessel 30, with this bed of catalyst defining a first or low temperature regeneration zone employed in the overall process. Hydrogen or the feed hydrocarbon having hydrogen dissolved therein is charged into the bottom of the first regeneration zone through line 32 and is then passed into a distribution means 33. The dissolved hydrogen will move upward through the dense bed of catalyst thereby coming into contact with all of the catalyst present within this regeneration zone. A portion of the regenerated catalyst present within the regeneration zone is withdrawn on a continuous basis from the regeneration zone through line 34 at a rate controlled by a slide valve 35 for passage into the bottom of the riser reaction zone. Hydrogen-free feed hydrocarbon is charged to the process through line 43 at a rate effective to seal the lower portion of conduit 34 to the downward passage of hydrogen-containing liquid. There is therefore a net upward flow of hydrogen-free liquid through conduit 34 which flushes hydrogen from the regenerated catalyst.

A smaller second portion of the catalyst present in the overall vessel 30 is withdrawn through line 36 at a rate controlled by valve 37. Line 36 preferably removes catalyst near the interface between the accumulated dense bed of catalyst and the liquid above it, which defines the border between the separation zone and the regeneration zone. The catalyst could be withdrawn at other points within the overall vessel 30 above or below this interface. This smaller stream of catalyst is passed into the high temperature regeneration zone 42 wherein it is contacted with a stream of liquid phase feed hydrocarbon containing dissolved hydrogen which is circulated into zone 42 through line 38 and removed through 39. This is the high temperature regeneration zone employed in the process and produces fully regenerated catalyst which is withdrawn through line 40 at a rate controlled by line 41 and passed into the vessel 30. This passage of the fully regenerated catalyst into the vessel 30 results in its admixture with the used catalyst present within vessel 30 and also with partially regenerated catalyst present within the vessel 30. The catalyst withdrawn through line 34 for passage into the riser reaction zone will therefore comprise an admixture of fully and partially regenerated catalyst.

Those skilled in the art will see that there are several alternative mechanical arrangements to this process flow, such as the passage of the fully regenerated catalyst directly into conduit 34 for admixture with the partially regenerated catalyst therein. In all of these concepts, however, the fully regenerated catalyst is admixed with partially regenerated catalyst prior to return to the reaction zone.

As used herein the term "substantially free" means a molar concentration less than 1.5 mole percent. The term "rich" is intended to indicate a concentration of the specified compound or class of compounds greater than 50 mole percent.

The inconvenience and increased cost associated with the vapor-phase regeneration employed in our prior embodiment has led to extensive developmental research and testing in an effort to eliminate the need for a vapor-phase regeneration. Some of the problems involved with this type of regeneration included the need to dry the catalyst to make it free flowing, the need to compress, heat, cool and condense various vapor streams, a necessity to seal and compartmentalize the process into liquid and vapor-phase sections operated at different conditions and a fairly high level of overall complexity. Extensive efforts were therefore directed at developing a suitable liquid-phase regeneration capable of replacing the vapor-phase regeneration of our prior process. One central factor in the regeneration is the ability to deliver to the catalyst the hydrogen required for the hydrogenative portion of regeneration. A liquid phase system is not as effective as a vapor-phase system in delivering hydrogen. However, recent experimentation has found that liquid phase isobutane can supply sufficient hydrogen at a pressure above 500 psig (3447 kPa).

Operation of the regeneration zone of a pilot plant at these high pressures resulted in the reaction zone also being at this high pressure. This led to the unexpected discovery that the activity of the preferred catalyst is significantly increased by the increased pressure. A pressure increase of from about 450 psig to 925 psig resulted in a 40 percent increase in catalyst activity.

The ability to perform liquid-phase regeneration has a number of other advantages over our prior process. For instance, it eliminates any need to fluidize the catalyst during the regeneration thus lowering catalyst particle attrition. A less complicated regeneration zone configuration also results.

In our earlier embodiment of this process, the portion of the used catalyst subjected to a more strenuous regeneration was confined within a separate regeneration zone for an average residence time of at least 30 minutes while being contacted with a heated stream of hydrogen and isobutane fed to the bottom of the regeneration zone. This hot hydrogen-hydrocarbon stripping removed liquid phase hydrocarbons and deposits from the catalyst and produced a vapor phase regeneration zone effluent stream. In the prior embodiment, this regeneration zone effluent stream is preferably cooled sufficiently to condense substantially all of the hydrocarbons contained within this stream and then subjected to vapor-liquid separation. The recovered liquids are passed into the products recovery zone and the hydrogen recycled to the bottom of the regeneration zone. Catalyst which has been subjected to this high temperature stripping is withdrawn from the regeneration vessel and cooled. Isobutane coolant is used to cool the catalyst to less than about 38° C. and the catalyst then flows into a stripping section to remove hydrogen. Catalyst cooling may be used to heat and/or vaporize the isobutane. Vaporization has some advantages with respect to heat integration. The majority of the catalyst collected in the bottom of the hydrocyclone separation zone passes downward through a liquid-filled wash section which functions as a mild regeneration zone. The descending catalyst preferably passes through a series of baffles intended to admix and stir the catalyst and promote uniform contacting of the descending catalyst with a rising stream of hydrogen saturated isobutane injected into the bottom of the wash section. The countercurrent contacting within the wash zone imparts a mild regeneration to the used catalyst descending from the hydrocyclone. The hydrogen saturated isobutane rises into the hydrocyclone and is removed with the product stream.

In the prior embodiment, the washed catalyst descending through the wash section enters a stripping section where it descends countercurrent to the rising hydrogen-free isobutane. A series of inclined conical or funnel-like baffles provided in the stripping zone at various locations ensures admixing of the rising isobutane with the descending catalyst and a thorough removal of hydrogen from the catalyst. At the midpoint of the stripping section, the descending catalyst stream from the wash section is joined and admixed with the stream of highly regenerated catalyst removed from the external regeneration zone. Additional cooling is provided to the bottom of the stripping section by means of indirect heat exchanger. This cooling results in the catalyst being brought to the desired reaction zone inlet temperature before passage into the riser. The upward flow of hydrogen-free isobutane is relied upon to flush hydrogen from the catalyst fed to the reactor.

The Drawing and above description are presented in terms of controlling catalyst flow through the use of slide valves. Alternative means can be used for this purpose including, for example, other types of valves, lockhoppers, fluid flow control (the reverse flow of liquid), screw conveyors, etc. One particular alternative is the use of an "L valve", which would reduce the amount of isobutane flush needed in the process.

In the subject embodiment of the process, all of the used catalyst from the separation zone flows into either a liquid-phase mild regeneration zone or a high temperature liquid-phase regeneration zone. The mild regeneration zone is capable of performing only a partial regeneration of the catalyst as by 5 removing surface deposits soluble in the feed hydrocarbon and some hydrogenation. The high temperature regeneration zone performs a complete hydrogenative regeneration requiring a minimum stoichiometric amount of hydrogen. This regeneration restores essentially all activity to the used catalyst.

The amount of hydrogen charged to the high temperature regeneration zone must be at least equal to the stoichiometrically required amount for the hydrogenation of the carbonaceous material present on the used catalyst entering the regeneration zone. For purposes of this calculation, it is assumed that the carbonaceous material is composed of monoolefinic octenes. The amount of hydrogen required for regeneration will therefore vary with the catalyst condition but can be easily calculated and controlled. An additional quantity of hydrogen, again equal to the stoichiometrically required amount, is charged to the low temperature regeneration zone. The regeneration performed in the low temperature regeneration zone is only capable of recovering about 90–95 percent of the activity of the preferred catalyst after use for motor fuel alkylation, which results in significant deactivation after a number of catalyst passes through the reaction zone. The regeneration in the high temperature regeneration zone will recover close to 100 percent of the catalyst's activity. Different results may be obtained for different catalysts.

The steps of the subject embodiment of our process include the partial regeneration of catalyst located in a first regeneration zone by contact with a liquid-phase hydrocarbon, which is preferably the feed hydrocarbon such as isobutane. Hydrogen is preferably dissolved in this liquid-phase stream up to the point of the stream being saturated with hydrogen. The average residence of catalyst particles in this liquid-phase hydrocarbon regeneration zone is preferably from about 0.5 to 20 minutes. The liquid-phase low temperature or mild regeneration is performed in a vessel or conduit in relatively open communication with the reaction zone. The temperature and pressure conditions employed in this regeneration zone will therefore be very similar to those in the reaction zone. The temperature in the low temperature regeneration zone will correspond to the outlet temperature of the reactor, with any required cooling being performed downstream. The temperature of the feed stream can be used to reduce the temperature of the regenerated catalyst. Further information on the regeneration of the preferred catalyst and the catalyst itself may be obtained from U.S. Pat. Nos. 5,310,713 and 5,391,527.

The subject process eliminates the "hydrogen stripping" or vapor-phase regeneration operation of our prior embodiment described in our prior application in which catalyst is contacted with a vapor-phase gas stream at an elevated temperature in the range of about 80 to about 500 degrees C. and more preferably from 100° to 250° C. The zone in which this "hydrogen stripping" or severe regeneration step of our prior embodiment is performed is operated in a manner which provides a longer average residence time for the catalyst particles than the liquid-phase regeneration step of this embodiment. The average residence time of a catalyst particle in the vapor-phase zone was at least 30 minutes and can reach about 12 to 24 hours. This regeneration step is performed using a vapor-phase hydrogen rich gas stream. The presence of some isobutane in this gas stream may be desirable to increase the heat capacity of the gas and therefore increase catalyst heat up rates. The longer residence time required for this regeneration step allows the high temperature gas charged to the regeneration zone to vaporize liquid Which flows into the severe regeneration zone. This "hydrogen-stripping" regeneration is not employed in the subject embodiment of our process.

All of the catalyst passing from the separation zone to the bottom of the riser is subject to one, and possibly both, of the two forms of regeneration. A much smaller quantity of catalyst flows through the high temperature regeneration zone compared to the flow through the low temperature regeneration zone. The flow through the high temperature regeneration zone will be only about 0.2 to about 30 weight percent, and preferably from about 10 to about 20 weight percent of the total catalyst flow through the riser.

In contrast to the low temperature regeneration zone, the high temperature regeneration zone is operated at conditions independent from the reaction zone. The pressure in the high temperature regeneration zone is preferably substantially the same as in the rest of the process, with minor differences being caused by differing elevations and flow induced pressure drops. The maximum temperature in the high temperature regeneration zone will be set by the critical temperature of the feed hydrocarbon. For motor fuel alkylation, this results in a maximum operating temperature of about 270° F. The combination of pressure and temperature are controlled to avoid the presence of two phase conditions. That is, no vapor should be present in this or any other part of the process, and it is presently preferred to avoid supercritical conditions even though this may be considered a single phase. The average temperature in the high temperature regeneration zone should be at least 50 degrees (F) above the outlet temperature of the reaction zone and is preferably 70-100 degrees higher.

The catalyst flow into the bottom of the riser is preferably as close to a continuous steady state flow as the equipment and catalyst system allow. The flow can, however, be in the form of numerous small quantities of catalyst transferred in rapid sequence.

The embodiment shown in the Drawing may also be varied by the use of heat exchangers to heat used catalyst and by the use of coolants in the high temperature regeneration zone. While the use of isobutane as coolant and integration with the product fractionation zone is preferred, other coolants including water, air or other hydrocarbons can be employed in a vapor phase regeneration. A further variation encompasses the use of countercurrent fluid flow to simultaneously cool newly regenerated catalyst and to flush hydrogen from the catalyst and liquid surrounding the catalyst.

The subject process can be performed using any solid, that is, heterogeneous, catalyst which is stable and has the required activity and selectivity for the desired reaction at the conditions needed to maintain liquid-phase reactants in the reaction zone. A large number of catalysts have been proposed for the production of motor fuel by alkylation including various zeolites and superacid catalysts. For instance, U.S. Pat. No. 4,384,161 describes the use of a large pore zeolite and a Lewis acid. The zeolites referred to include ZSM-4, ZSM-3, the faujasites including zeolite Y and mordenite. The Lewis acids mentioned in this reference include boron trifluoride and aluminum chloride. The alkylation of isoparaffins using a somewhat similar catalyst system comprising a large pore crystalline molecular sieve such as a pillared silicate or an aluminophosphate or silicoaluminophosphate together with a gaseous Lewis acid is disclosed in U.S. Pat. No. 4,935,577. The use of these Lewis acids is not preferred in the subject process as they provide their own waste handling and safety problems. They also will probably require provisions for the circulation of the Lewis acid, which may complicate the process as shown by the teaching of the just cited U.S. Pat. No. 4,935,577. U.S. Pat. No. 5,157,200 describes an isoparaffin alkylation process using a catalyst comprising a crystalline transition alumina, preferably eta or gamma alumina, which has been treated with a Lewis acid under anhydrous conditions. Previously referred to U.S. Pat. No. 5,157,196 describes an isoparaffin alkylation process using a slurried solid catalyst, with the preferred catalyst being an acid washed silica which has been treated with antimony pentafluoride. Both of these last two references describe a number of prior art solid bed paraffin alkylation catalysts.

A preferred paraffin alkylation catalyst comprises a refractory inorganic oxide impregnated with a monovalent cation, especially an alkali metal cation or an alkaline earth metal cation, and whose bound surface hydroxyl groups have been at least partially reacted with a Friedel-Crafts metal halide. Analogs of these catalysts without the metal cations are described in U.S. Pat. Nos. 2,999,074 and 3,318,820 which describe preparation techniques which can be applied to the preferred catalysts. The preferred refractory oxide is alumina having a surface area greater than 50 $m^2/g$, but the use of other oxides including titania, zirconia, silica, boria and aluminum phosphate is contemplated. The preferred catalyst also contains a metal component active for olefin hydrogenation deposited on the inorganic oxide prior to reaction of the bound surface hydroxyl groups with the metal halides. This metal may be chosen from the group consisting of nickel, platinum, palladium, and ruthenium with the first three of these metals being preferred. The catalyst contains one or more monovalent metal or alkaline earth metal cations selected from the group consisting of lithium, sodium, potassium, cesium, silver, copper, beryllium, magnesium, calcium and barium. Subsequent to the deposition of these metals and the controlled calcination of the composite, the composite is reacted with a Friedel-Crafts metal halide. The metal may be aluminum, zirconium, tin, tantalum, gallium, antimony or boron. Suitable halides are the fluorides, chlorides and bromides. This preferred catalyst has been found to be sensitive to low levels of water as may be generated from oxygenates in the feed streams. Very low levels of such oxygenates as butanols are therefore important to catalyst life and successful process operation.

The presence of a highly active metal hydrogenation component on the catalyst will promote hydrogenation of the feed olefin if both the olefin and hydrogen simultaneously contact the catalyst. This potential waste of the olefin and hydrogen can be avoided by careful design and operation of the process to avoid having both the olefin and hydrogen in simultaneous contact with the catalyst. This can be done by flushing the hydrogen or olefin from the catalyst before inserting it into a zone containing the other compound as described above.

Silicalites have been described as useful alkylation catalysts for the production of monoalkylbenzenes in U.S. Pat. No. 4,489,214 to J. R. Butler et al. and as useful in methylating toluene to produce paraxylene in U.S. Pat. No. 4,444,989 issued to F. E. Herkes. The use of ZSM-5 zeolites in aromatic alkylation is described in U.S. Pat. No. 3,751, 506. ZSM-5 zeolites that have been treated with one or more compounds or elements to improve their selectivity for para-selective alkylation of aromatic hydrocarbons are described in U.S. Pat. No. 4,420,418. The use of zeolite L, zeolite Omega and zeolite beta as alkylation catalysts for the selective alkylation of benzene is described in U.S. Pat. No. 4,301,316. The use of a number of natural and synthetic zeolites including clinoptilolite and zeolite Y as alkylation catalysts is described in U.S. Pat. No. 3,251,897.

The catalyst may be in the form of any suitable shape and size which results in a solid catalyst which flows readily in both dry and wet states and which is readily fluidized at the moderate liquid flow rates employed in the riser. The catalyst can therefore be present as small irregular particles or as uniformly shaped particles. It is preferred that the catalyst is present as "microspheres" having an average diameter less than about 0.16 cm and more preferably less than about 0.08 cm.

Suitable operating conditions for the reaction zone include an outlet temperature of about −17 to 77 degrees C. (0°–170° F.), preferably 10 to 38 degrees C. (50°–100° F.), and a pressure as required to maintain the hydrocarbons present as a liquid. However a moderately elevated pressure above that required for liquid phase operation in the general range of about 2410 to about 6500 kPa (350–950 psig) is preferred with a pressure greater than 3447 kPa (500 psig) being highly preferred. These outlet temperatures assume an approximate 20°–50° F. degree temperature rise while the catalyst traverses the length of the reactor, which depends greatly on such factors as the amount of olefin in the feed stream, etc. The rate of catalyst flow in the riser and its size are best described in terms of catalyst to olefin ratio and residence time. The catalyst to olefin weight ratio can be within the broad range of about 1:1 to about 1:25 and is preferably between 3:1 and 15:1. The residence time of the catalyst and the hydrocarbon in the reaction zone will be quite similar and can vary within the broad range of 5 seconds to 20 minutes, with a residence time greater than 20 seconds being preferred. The riser reaction zone is preferably designed and operated in a manner intended to promote plug flow (limited backmixing) of the reactants, products and catalyst within the riser. However, the liquid must flow upward faster than the catalyst in order to transport it.

It is generally preferred that the reaction zone is operated with an excess of the feed hydrocarbon compared to the alkylating agent. That is, it is preferred to operate with a ratio of the feed paraffinic or aromatic hydrocarbon to a feed olefin at the reactor entrance greater than 1:1, and preferably from about 2:1 to about 5:1 or higher as measured by the flow rates into the reaction zone. It is highly preferred to operate with an abundance of isoparaffin compared to alkylating agent in a motor fuel alkylation process. Specifically, it is preferred that the molar ratio of isoparaffin to olefin being charged to the reaction zone is greater than 2:1 and more preferably greater than 3:1. Ratios from 10:1 to about 100:1 or higher can be employed for motor fuel alkylation. Additional quantities of the olefin may be charged to the reaction zone at a number of points along the flow path of the feed hydrocarbon to maintain a higher average paraffin to olefin ratio.

Provisions may be made for removing used catalyst from the reaction zone and for replacement of the used catalyst with fresh (unused) catalyst. Conventional valved lockhopper systems may be used for this purpose.

The previously preferred embodiment of our invention was characterized as a process for the alkylation of a feed hydrocarbon which comprises the steps of passing a first catalyst stream, comprising regenerated catalyst, and a feed stream comprising the feed hydrocarbon and an alkylating agent into the bottom of a vertical riser-reaction zone maintained at reaction conditions and producing a reaction zone effluent stream comprising used catalyst, the feed hydrocarbon and a product hydrocarbon; discharging the reaction zone effluent stream into a separation zone in which used catalyst is separated from the liquid phase product hydrocarbon and thereby forming a liquid-phase separation zone effluent stream comprising the feed and product hydrocarbons, with the thus separated used catalyst descending downward within the separation zone; transferring a major first portion of the used catalyst downward through a mild regeneration zone wherein the used catalyst is countercurrently contacted with feed hydrocarbon containing dissolved hydrogen and withdrawing catalyst from the mild regeneration zone as a second catalyst stream; transferring the remaining second portion of the used catalyst downward from the separation zone into a high temperature regeneration zone wherein the used catalyst is contacted with vapor phase hydrogen at vapor phase regeneration conditions and withdrawing catalyst from the high temperature regeneration zone as a third catalyst stream; commingling the second and third catalyst streams to form the first stream of catalyst; countercurrently contacting the first stream of catalyst with the feed hydrocarbon to remove hydrogen from the catalyst; and, recovering the product hydrocarbon from the separation zone effluent stream.

With the discovery that a fluidized vapor-phase high temperature regeneration zone could be replaced by a high pressure, high temperature liquid-phase regeneration zone, the subject process may be characterized as a process for the alkylation of a feed hydrocarbon which comprises the steps of passing a first catalyst stream, comprising regenerated catalyst, and a feed stream comprising the feed hydrocarbon and an olefinic hydrocarbon into the bottom of a vertical riser-reaction zone maintained at reaction conditions which include a pressure above 400 and preferably above 500 psig and an outlet temperature of about 50° to about 100° F. and producing a reaction zone effluent stream comprising used catalyst, the feed hydrocarbon and a product alkylate hydrocarbon; discharging the reaction zone effluent stream into a vessel comprising an upper separation zone in which used catalyst is separated from the liquid phase product hydrocarbon and thereby forming a liquid-phase separation zone effluent stream comprising the feed and product alkylate hydrocarbons, with thus separated used catalyst descending downward within the vessel to form a dense bed of catalyst retained in a low temperature first regeneration zone located in a lower portion of the vessel; transferring a major first portion of the used catalyst downward through the first regeneration zone wherein the used catalyst is countercurrently contacted with a first stream of the feed hydrocarbon containing dissolved hydrogen, and withdrawing catalyst from the mild regeneration zone as a second catalyst stream; transferring the remaining second portion of the used catalyst downward from the separation zone into a high temperature second regeneration zone wherein the used catalyst is contacted with a second stream of the feed hydrocarbon hydrogen at regeneration conditions which include a temperature above 225° F. and a pressure essentially equal to the pressure in the reaction zone and withdrawing catalyst from the high temperature second regeneration zone as a third catalyst stream; commingling the second and third catalyst streams to form the first stream of catalyst, countercurrently contacting the first stream of catalyst with the feed hydrocarbon to remove hydrogen and hydrogen-containing liquid-phase hydrocarbons from the catalyst; recovering the product alkylate hydrocarbon from the separation zone effluent stream.

What is claimed:

1. A process for the alkylation of a feed hydrocarbon which comprises the steps:

a. passing a first catalyst stream, comprising regenerated catalyst withdrawn from a first regeneration zone, and a feed stream comprising the feed hydrocarbon and an alkylating agent into a vertical fluidized reaction zone maintained at reaction conditions including a pressure sufficient to maintain liquid-phase conditions and producing a reaction zone effluent stream comprising used catalyst, the feed hydrocarbon and a product hydrocarbon;

b. discharging the reaction zone effluent stream into a separation zone in which used catalyst is separated from liquid phase product hydrocarbon and thereby forming a liquid-phase separation zone effluent stream comprising the feed and product hydrocarbons, with the thus separated used catalyst descending downward within the separation zone;

c. transferring a major first portion of used catalyst downward through the liquid-phase first regeneration zone operated at conditions essentially equal to those maintained in the riser-reaction zone and wherein the used catalyst is contacted with the feed hydrocarbon and dissolved hydrogen to form partially regenerated catalyst, and removing said partially regenerated catalyst from the regeneration zone as a second catalyst stream;

d. transferring a smaller second portion of used catalyst into a liquid-phase second regeneration zone operated at a pressure substantially equal to the pressure in the riser-reaction zone and wherein the used catalyst is contacted with a liquid-phase regeneration stream comprising dissolved hydrogen at high temperature liquid-phase regeneration conditions, including a temperature at least about 50° F. above the outlet temperature of the reaction zone, and withdrawing catalyst from the second regeneration zone as a third catalyst stream;

e. admixing the third catalyst stream with partially regenerated catalyst; and f. recovering the product hydrocarbon from the separation zone effluent stream.

2. The process of claim 1 wherein the third catalyst stream is admixed with partially regenerated catalyst by passing the third catalyst stream into the separation zone.

3. The process of claim 1 wherein the third catalyst stream is admixed with partially regenerated catalyst by passing the third catalyst stream into the first regeneration zone.

4. The process of claim 1 wherein the third catalyst stream is admixed with partially regenerated catalyst by admixture with the second catalyst stream.

5. The process of claim 1 wherein the catalyst is spherical.

6. The process of claim 1 wherein the feed hydrocarbon is an aromatic hydrocarbon.

7. The process of claim 1 wherein the feed hydrocarbon is an paraffinic hydrocarbon.

8. The process of claim 1 wherein the alkylating agent is an olefinic hydrocarbon.

9. The process of claim 1 wherein the feed hydrocarbon is an aromatic hydrocarbon and the alkylating agent is a monohydric alcohol.

10. A process for the alkylation of a feed hydrocarbon comprising a $C_3$ to $C_5$ paraffin which comprises the steps:

a. passing a first catalyst stream, comprising regenerated catalyst, the feed hydrocarbon and a feed stream comprising an alkylating agent into a vertical riser-reaction zone maintained at reaction conditions including a temperature of less than 100° F. and a pressure above 400 psig and producing a reaction zone effluent stream comprising used catalyst, the feed hydrocarbon and a product hydrocarbon;

b. discharging the reaction zone effluent stream into a vessel comprising an upper separation zone in which used catalyst is separated from the majority of the liquid phase product hydrocarbon and thereby forming a liquid-phase separation zone effluent stream comprising the feed and product hydrocarbons, with the thus separated used catalyst descending downward to form a dense bed of catalyst retained in a low temperature first regeneration zone wherein the used catalyst is contacted with feed hydrocarbon containing dissolved hydrogen at low temperature liquid-phase regeneration conditions essentially equal to the conditions maintained in the riser-reaction zone and forming partially regenerated catalyst which is withdrawn from the first regeneration zone and mixed with the feed stream;

c. transferring a second catalyst stream, comprising an aliquot first portion of the used catalyst, from said vessel through a transfer conduit into a high temperature second regeneration zone wherein the used catalyst is contacted with liquid-phase feed hydrocarbon containing dissolved hydrogen at high temperature liquid phase regeneration conditions which include a temperature from about 200° to about 250° F., and withdrawing catalyst from the high temperature second regeneration zone as a third catalyst stream;

d. admixing the third catalyst stream with used catalyst or with partially regenerated catalyst; and e. recovering the product hydrocarbon from the separation zone effluent stream.

11. The process of claim 10 wherein the feed hydrocarbon is a paraffinic hydrocarbon.

* * * * *